US007801270B2

(12) United States Patent
Nord et al.

(10) Patent No.: US 7,801,270 B2
(45) Date of Patent: Sep. 21, 2010

(54) TREATMENT PLAN OPTIMIZATION METHOD FOR RADIATION THERAPY

(75) Inventors: Janne Ilmari Nord, Espoo (FI); Jarkko Y. Peltola, Tuusula (FI)

(73) Assignee: Varian Medical Systems International AG, Zug (CH)

( * ) Notice: Subject to any disclaimer, the term of this patent is extended or adjusted under 35 U.S.C. 154(b) by 131 days.

(21) Appl. No.: 12/142,181

(22) Filed: Jun. 19, 2008

(65) Prior Publication Data

US 2009/0316858 A1 Dec. 24, 2009

(51) Int. Cl.
*A61N 5/10* (2006.01)
(52) U.S. Cl. ....................................... 378/65
(58) Field of Classification Search ................ 378/65
See application file for complete search history.

(56) References Cited

U.S. PATENT DOCUMENTS

| 6,879,659 | B2* | 4/2005 | Alber ............................ 378/65 |
| 2006/0045238 | A1* | 3/2006 | Nguyen ........................ 378/65 |
| 2007/0003011 | A1* | 1/2007 | Lane ............................. 378/65 |
| 2007/0081629 | A1* | 4/2007 | Yin et al. ...................... 378/65 |

FOREIGN PATENT DOCUMENTS

WO   WO 2005/035061 A2   4/2005

OTHER PUBLICATIONS

Spirou et al., "A gradient inverse planning algorithm with dose-volume constraints", Medical Physics, vol. 25, Issue 3, (Mar. 1998), pp. 321-333.*
International Search Report and Written Opinion of the International Searching Authority of May 11, 2010.

* cited by examiner

*Primary Examiner*—Chih-Cheng G Kao
(74) *Attorney, Agent, or Firm*—Townsend and Townsend and Crew LLP

(57) ABSTRACT

A treatment planning method and system for optimizing a treatment plan used to irradiate a treatment volume including a target volume, such as a tumor, is disclosed. In accordance with the present invention, gradients of a cost function that defines a treatment volume are back projected to a surface of interest. The method and system of preferred embodiments of the present invention calculate the gradients with respect to the dose received by the treatment volume. Machine parameters that are associated with the surface of interest may then be optimized based on the back projected gradients.

24 Claims, 4 Drawing Sheets

TREATMENT PLAN OPTIMIZATION METHOD FOR RADIATION THERAPY

The present invention relates generally to treatment planning for radiation therapy and is more particularly directed to methods of calculating and optimizing a treatment plan.

BACKGROUND OF THE INVENTION

In general, radiation therapy consists of the use of ionizing radiation to treat living tissue, usually tumors. There are many different types of ionizing radiation used in radiation therapy, including high energy x-rays, electron beams, and proton beams. However, the process of administering the radiation to a patient can be somewhat generalized regardless of the type of radiation used.

Modern radiation therapy techniques include the use of Intensity Modulated Radiotherapy ("IMRT"), typically by means of a radiotherapy system, such as a linear accelerator, equipped with a multileaf collimator ("MLC"). Use of multileaf collimators in general, and IMRT in particular, allows the radiologist to treat a patient from multiple angles while varying the shape and dose of the radiation beam, thereby providing greatly enhanced ability to deliver radiation to a target within a treatment volume while avoiding excess irradiation of nearby healthy tissue. However, the greater freedom which IMRT and other complex radiotherapy techniques, such as volumetric modulated arc therapy (where the system gantry moves while radiation is delivered) and three-dimensional conformal radiotherapy ("3D conformal" or "3DCRT"), afford to radiologists has made the task of developing treatment plans more difficult. As used herein, the term radiotherapy should be broadly construed and is intended to include various techniques used to irradiate a patient, including use of photons (such as high energy x-rays and gamma rays), particles (such as electron and proton beams), and radiosurgical techniques. While modern linear accelerators use MLCs, other methods of providing conformal radiation to a target volume are known and are within the scope of the present invention.

Treatment planning starts typically with (1) images of the treatment volume (e.g., slices from CT or MRI scans) and, (2) the desired dose of radiation which is to be delivered to a target, such as a tumor, within the treatment volume, and (3) the maximum dose which can be safely absorbed by tissue structures, such as organs, within the treatment volume that are adjacent to or near the tumor or other target volume. As used herein, the term "treatment volume" is used to refer to the entire volume that will be subjected to radiation, and is sometimes referred to as the "irradiated volume." The target volume, intended to receive a therapeutic prescribed dose, is sometimes referred to as the "planning target volume" ("PTV"). Both the target within the treatment volume and any nearby organs may have complex three dimensional shapes adding to the difficulty of preparing a treatment plan.

A variety of algorithms have been developed to solve the "inverse problem" of devising and optimizing a specific, three-dimensional treatment plan for irradiating the treatment volume from a variety of angles or, in arc therapy, while the system gantry is moving, to deliver a desired radiation dose to the target while minimizing irradiation of nearby tissue, taking into account the capabilities and physical limitations of the radiotherapy system. Generally speaking, the inverse problem involves optimizing the angles, MLC leaf movements and durations of irradiations. Because of the large number of variables involved and complex matrix manipulations that are required, the algorithms for calculating and optimizing treatment plans require substantial computational time even when using modern high speed computers.

Generally two types of algorithms are used in treatment planning: (1) dose calculations algorithms based on a given set system parameters, e.g., gantry angle, MLC leaf positions, etc., and (2) search algorithms which use various techniques to adjust system parameters between dose calculations to achieve optimization of the plan. Some exemplary dose calculation algorithms include various Monte Carlo ("MC") techniques and pencil beam convolution ("PBC"). Some exemplary search algorithms include various stochastic and deterministic methods, including various simulated annealing ("SA") techniques, algebraic inverse treatment planning ("AITP"), and simultaneous iterative inverse treatment planning ("SIITP"). Such techniques, and others, are well known in the art, and each of the techniques has advantages and disadvantages relative to the others. Each of the methods requires iterative dose calculations for optimization, and generally a high number of dose calculation iterations or "passes" are required to converge on an optimal plan. Typically, each iteration involves changing the boundary conditions using the search algorithm and recalculating the dose distribution. While a fully optimized plan might be achieved using known methods if adequate time is available, as a practical matter time constraints often limit the ability to achieve this goal.

It is noted that a treatment plan is typically implemented over a time period. Thus, the patient typically is given multiple treatments over the course of days or weeks, such that the dose delivered to the treatment volume is fractionated. During the time between treatments changes may occur in the treatment volume, for example, the tumor being irradiated may shrink in size or surrounding organs may change position. Any such changes may necessitate revising and re-optimizing the treatment plan before the next fractionated dose is delivered. The problem of re-optimizing a treatment plan is known, and presents somewhat different issues than achieving an initially optimized plan as described herein.

Treatment planning algorithms may be implemented as part of an overall, integrated treatment planning software package which provides additional features and capabilities. For example, a dose calculation algorithm and search algorithm may be used to optimize a set of fluence maps at each gantry angle, with a separate leaf sequencer used to calculate the leaf movements needed to deliver them. Alternatively, a dose calculation algorithm and search algorithm may be used to directly optimize leaf movements and other machine parameters. The Eclipse™ Treatment Planning System offered by the assignee of the present invention includes such an integrated software program.

Accordingly, there is a need for improved systems and methods to efficiently perform direct machine parameter optimization to optimize a radiotherapy treatment plan.

BRIEF SUMMARY OF THE INVENTION

The present invention is directed to a method and system for optimizing a treatment plan for irradiating a treatment volume which includes a target volume. In accordance with the present invention, gradients of a cost function that define a treatment volume are back projected to a surface of interest. Specifically, the method and system of some embodiments of the present invention calculate the gradients with respect to the dose received by the treatment volume.

One embodiment of the present invention comprises a method of optimizing a treatment plan for irradiating a treatment volume within a patient. The method may include the step of establishing at least one treatment parameter. The method may further include the step of establishing a cost function that corresponds to the treatment volume, wherein the treatment volume includes a target volume intended to receive a therapeutic dose of radiation and a non-target volume, intended to receive a smaller dose of radiation. The gradients of the cost function can be calculated and back projected to a surface that can be an optimization surface. The gradients may be responsive to changes in the at least one treatment parameter, and the optimization surface can be defined by the at least one treatment parameter. The method can further comprise normalizing the back projected gradients within the optimization surface. Normalizing the back projections can comprise grouping the back projections into groups that are competing for changes in treatment parameters, where the treatment parameters affect how the cost function gradients back project onto the optimization surface. The method may further comprise changing a treatment parameter and iterating the previous steps a plurality of times.

Another embodiment of the present invention comprises a method for generating a radiation therapy treatment plan. The method may include the step of establishing a treatment machine parameter. The method may further include the step of establishing a treatment volume. The treatment volume may include a target volume, intended to receive a therapeutic dose of radiation and a non-target volume, intended to receive a smaller dose of radiation. The method may further include establishing a cost function for the treatment volume, where the cost function may be based on the dose of radiation received by the treatment volume. The method may further include the step of back projecting the gradients of the cost function to a surface, where the gradients are calculated with respect to the dose that is received by the treatment volume. The surface may be a surface that is defined by a treatment machine parameter. The surface may be segmented into a matrix with multiple elements, and the gradient back projections that project into each of the elements may be aggregated. The matrix elements can be grouped such that the groups are competing for changes in the machine parameter. The machine parameter may then be changed to optimize the groups. These steps may be repeated a plurality of times.

In yet another embodiment of the present invention, the embodiment may comprise a method for optimizing leaf positions of a multi-leaf collimator used to deliver a radiation treatment plan to a patient. The method may comprise establishing an initial position for a plurality of leaves of a multi-leaf collimator. The method may further comprise establishing a cost function for a treatment volume, wherein the treatment volume may include a target volume, intended to receive a therapeutic dose of radiation and a non-target volume, intended to receive a smaller dose of radiation. The method may further include establishing a cost function based on a dose of radiation received by the treatment volume. The method may further comprise back projecting gradients of the cost function to a plane established by the leaves of the multi-leaf collimator. The gradients may be calculated with respect to the dose received by the treatment volume. The method may further comprise establishing a matrix in the plane established by the leaves of the multi-leaf collimator, wherein each element of the matrix corresponds to a leaf. The gradients that project into each of the elements may then be aggregated. The elements may then further be grouped into groups, wherein the groups may compete for position of the leaves of the multi leaf collimator. The position of the leaves may then be changed to optimize the groups. This process may be repeated a plurality of times.

Another embodiment of the present invention can comprise a computer readable medium. The computer readable medium may contain a program that can be executed by a computer. The program may contain code for performing the following steps. The steps may include the step of establishing at least one treatment parameter. The steps may further include the step of establishing a cost function that corresponds to the treatment volume, wherein the treatment volume includes a target volume intended to receive a therapeutic dose of radiation and a non-target volume, intended to receive a smaller dose of radiation. The gradients of the cost function can be calculated and back projected to a surface that can be an optimization surface. The gradients may be responsive to changes in the at least one treatment parameter, and the optimization surface can be defined by the at least one treatment parameter. The steps can further comprise normalizing the back projected gradients within the optimization surface. Normalizing the back projections can comprise grouping the back projections into groups that are competing for changes in treatment parameters, where the treatment parameters affect how the cost function gradients back project onto the optimization surface. The steps may further comprise changing a treatment parameter and iterating the previous steps a plurality of times.

These and other embodiments of the invention are described in further detail below.

DETAILED DESCRIPTION

Figure 1A:
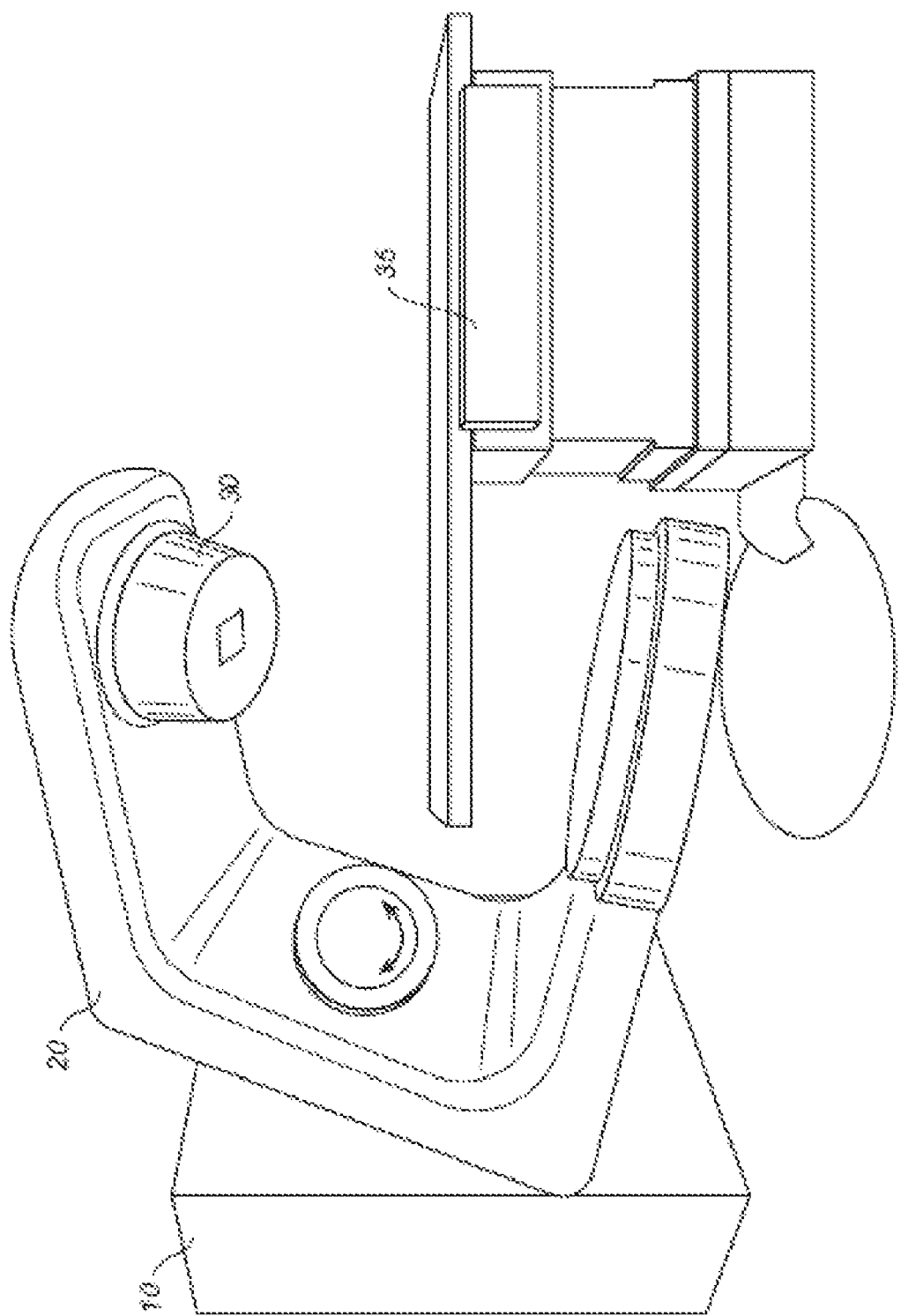
FIGS. 1A and 1B are perspective and side views of a radiation therapy system, as known in the prior art, of the type which may be used in connection with the present invention.
Figure 1B:
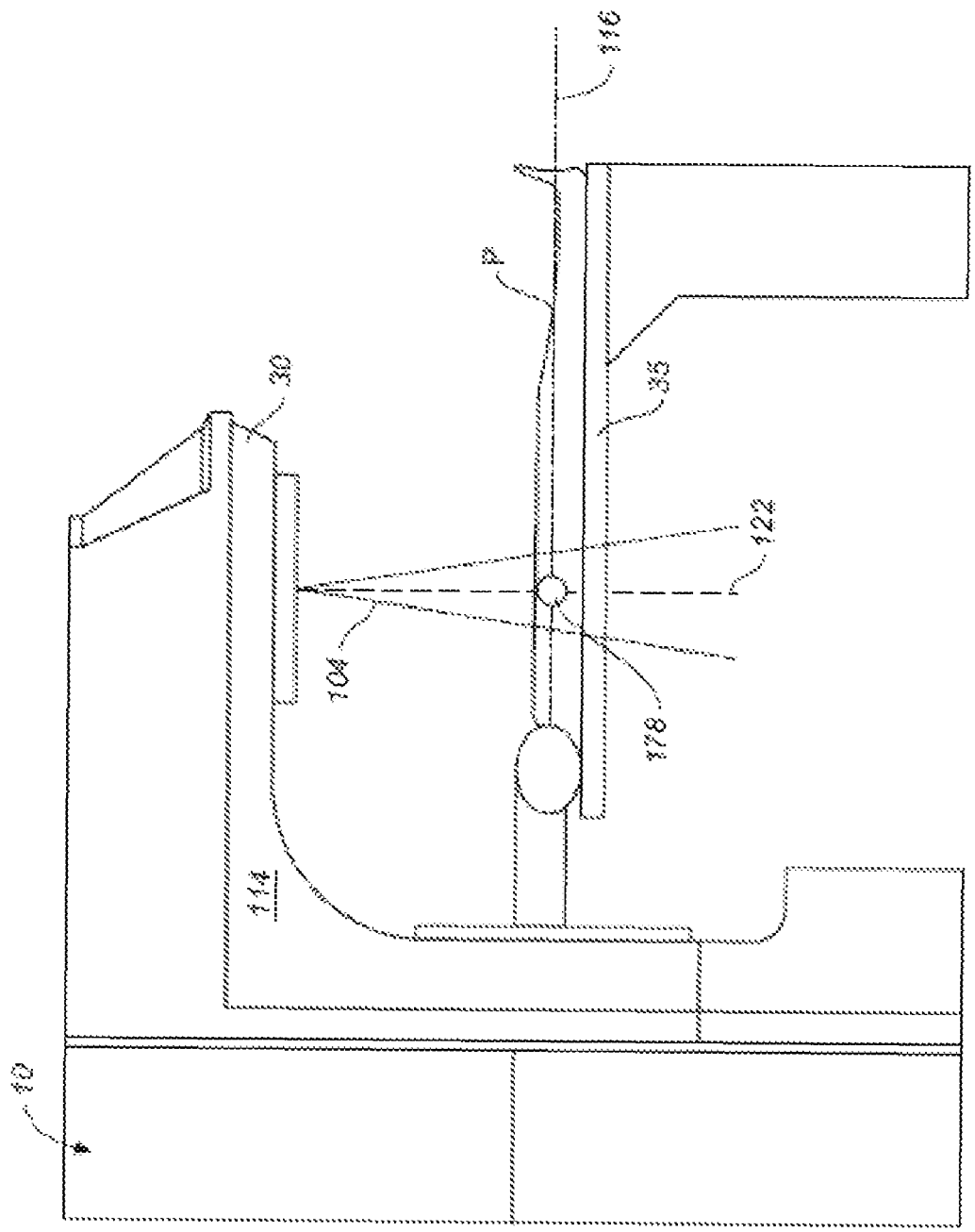

FIGS. 1A and 1B depict a radiation therapy system of the type which may be used in connection with the present invention. Referring to FIG. 1A, a perspective view of radiation therapy system (in this case a linear accelerator) is shown. Typically, such a system is capable of generating either an electron (particle) beam or an x-ray (photon) beam for use in the radiotherapy treatment of patients on a treatment table 35. Other radiation therapy systems are capable of generating heavy ion particles such as protons. For purposes of the present discussion, only x-ray irradiation will be discussed. However, it will be appreciated by those skilled in the art that the same principles apply to other systems.

Stand 10 supports a rotatable gantry 20 with a treatment head 30. Next to stand 10 there is arranged a control unit (not shown) which includes operational electronics for controlling the different modes of operation of the accelerator. A high voltage source is provided within the stand or in the gantry, to supply voltage to an electron gun (not shown) positioned on an accelerator guide located in gantry 20. Electrons are emitted from the electron gun into the guide (not shown) where they are accelerated. A source supplies RF (microwave) power for the generation of an electric field within the waveguide. The electrons emitted from the electron gun are accelerated in the waveguide by the electric field, and exit the waveguide as a high energy electron beam, typically at megavoltage energies. The electron beam then strikes a suitable metal target, emitting high energy x-rays in the forward direction.

Referring now to FIG. 1B, a somewhat more detailed side view of a radiation therapy system of the type which may be used in connection with the present invention is shown. A patient P is shown lying on treatment table 35. X-rays formed as described above are emitted from the target in treatment head 30 in a divergent beam 104. Typically, a patient plane 116, which is perpendicular to the page in FIG. 1B, is positioned about one meter from the x-ray source or target, and the axis of gantry 20 is located on plane 116, such that the distance between the target and isocenter 178 remains constant when gantry 20 is rotated. Isocenter 178 is at the intersection between patient plane 116 and the central axis of beam 122. A treatment volume to be irradiated is located about the isocenter.

"Jaws" (not shown) or x-ray collimators comprising an x-ray blocking material, are positioned in head 30 to define the width of the x-ray beam at the patient plane. Typically, the jaws are moveable and, when fully open, define a maximum beam of about 40 cm×40 cm at patient plane 116. A multileaf collimator ("MLC") (not shown in FIG. 1B) is positioned at the exit of head 30, to further shape the x-ray beam. Since its introduction in 1990 the MLC has become a standard feature of most radiation therapy systems. Current MLCs sold by the assignee of the present invention use up to 120 individually controllable leaves, typically thin slices of tungsten, that can be moved into or out of the x-ray beam under the control of system software. The MLC can be used to collimate the x-rays to provide conformal treatment of tumors from various angles ("3D conformal,") as well as intensity modulated radiotherapy ("IMRT"), whereby different radiation doses are delivered to different portions of the treatment area. The treatment volume, i.e., the irradiated volume proximate to the isocenter in the path of the x-ray beam, is defined by the jaws, the angle of the head and the MLC. In IMRT the leaves of the MLC are moved, such that the treatment volume comprises the total volume exposed during the course of a treatment. In arc therapy, the gantry is moved while radiation is delivered.

Modern radiation therapy techniques involve the use of a treatment plan designed to irradiate a desired target volume, usually corresponding to a tumor, with a desired dose of x-rays (or other radiation). Most treatment planning involves the use of the MLC to provide conformal and/or intensity modulated irradiation. Generally speaking, a treatment plan comprises irradiating one or more selected portions of the treatment volume with a calculated dose of x-rays, and often involves irradiating a treatment area from a plurality of different angles which, in the case of arc therapy, may be delivered while the gantry is rotated. Various treatment planning software and other tools are available for developing specific treatment plans, and the details of the various techniques for creating such plans are known and will be described in further detail below. Again, generally speaking, after a treatment plan is created it is implemented, in part, by controlling the angle of incidence and the leaves of the MLC so as allow the desired radiation dose to reach the selected portions of the treatment volume from the selected angles or while the gantry is rotating. In the simplest type of treatment plan, the MLC is adjusted to provide static conformal irradiation of a specific site from a single angle. In more complex plans, the leaves are moved into different positions between or during irradiations. The leaves of the MLC can either be moved iteratively into different positions while the beam is off, with irradiation between movements, (such that the leaves are static during x-ray emission), or they can be continually moved during irradiation in a "sliding window" or other variable aperture technique. As noted above, an important aspect of the conformal and IMRT techniques that are associated with the use of MLCs is the ability to both provide a desired dose of radiation to a target volume while minimizing the dose delivered to adjacent healthy tissue.

As described in more detail in the Background section above, several techniques have been developed to create treatment plans for IMRT or conformal radiation therapy. Generally, these techniques are directed to solving the "inverse" problem of determining the optimal combination of angles, radiation doses and MLC leaf movements to deliver the desired total radiation dose to the target while minimizing irradiation of healthy tissue. This inverse problem is even more complex for developing arc therapy plans where the gantry is in motion while irradiating the target volume. Heretofore, radiation oncologists or other medical professionals, such as medical physicists and dosimetrists, have used one of the available algorithms to develop and optimize a treatment plan. Typically, such planning starts with volumetric information about the target tumor and about any nearby tissue structures. For example, such information may comprise a map of the planning target volume ("PTV"), such as a prostate tumor, which is prescribed by the physician to receive a certain therapeutic radiation dose with allowable tolerances. Volumetric information about nearby tissues may include for example, maps of the patient's bladder, spinal cord and rectum, each of which may be deemed an organ at risk that can only receive a much lower, maximum prescribed amount of radiation without risk of damage. This volumetric information along with the prescribed dose limits and similar objectives set by the medical professionals is the basis for calculating an optimized dose distribution and the treatment plan to deliver it. The volumetric information may, for example, be reduced to an objective function or a single figure of merit that accounts for the relative importance of various trade-offs inherent in such a plan, along with constraints that must be met for the plan to be medically acceptable or physically possible.

Treatment planning algorithms must account for the capabilities of the specific radiation therapy system they are used with. For example, the type, energy level and fluence of the radiation beam, and the capabilities of the MLC. Generally speaking, treatment planning algorithms proceed by calculating the radiation dose received by each voxel in the treatment volume, adjusting one or more variable system parameters, such as the angle of irradiation or the positions of the MLC leaves, and then recalculating the dose received by each voxel. This process is ideally performed iteratively until an optimized plan is reached. However, the amount of time needed to perform the large number of calculations for each iteration places a practical limit on the number of iterations that can be performed. Accordingly, the algorithm is terminated after a predetermined amount of time, after a predetermined number of iterations, or after some other practical limit is reached. Generally speaking, there is a trade-off between the accuracy and speed of the different algorithms available for treatment planning.

Figure 2:
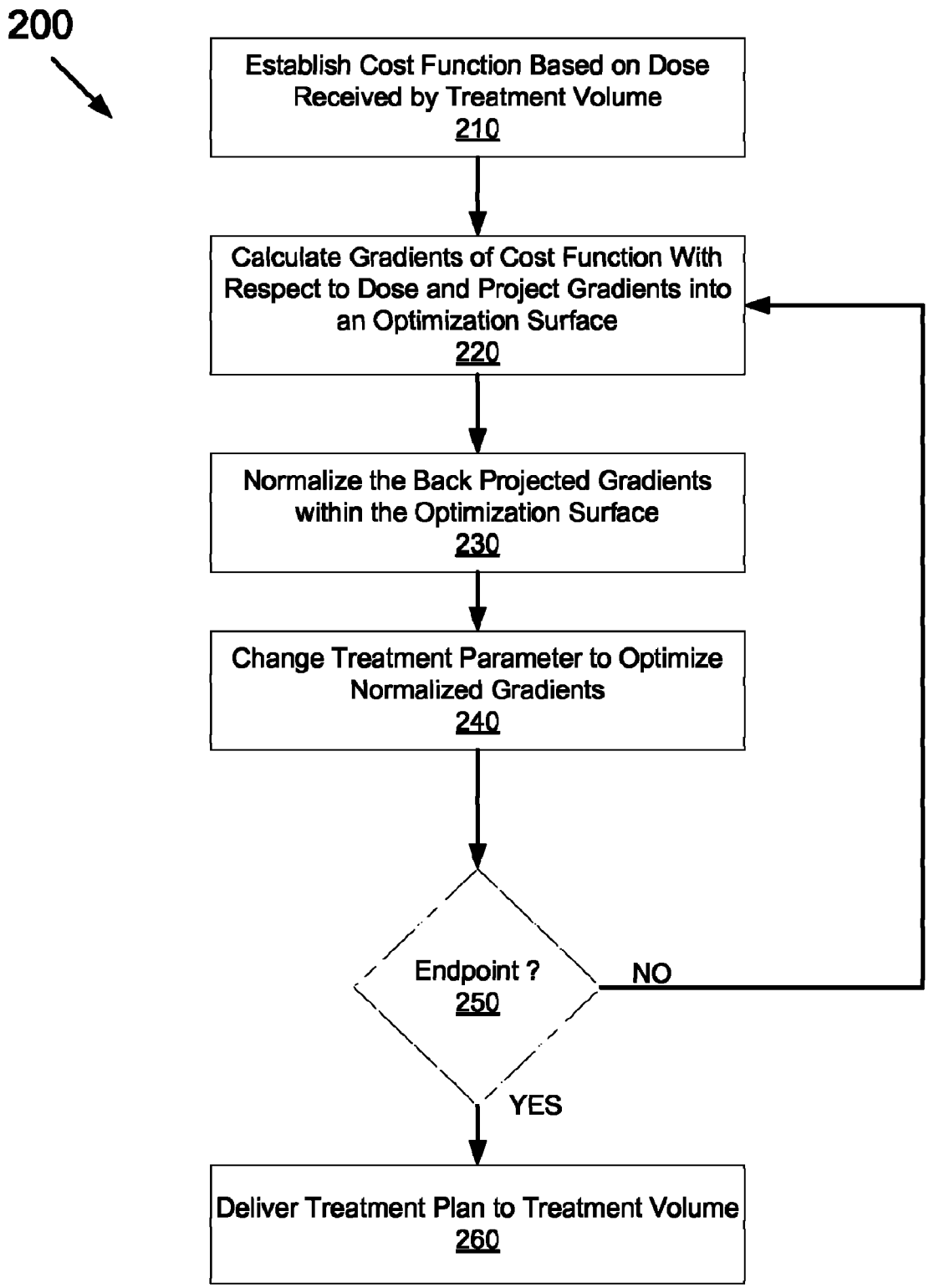
FIG. 2 is a flow chart in accordance with an embodiment of the present invention.

FIG. 2 is a flow chart 200 showing the steps of a general embodiment of the method of the present invention. The overall aim of the inventive method is to develop an optimized treatment plan for irradiating a treatment volume such that the target volume or tumor receives a prescribed dose of radiation, while limiting irradiation of adjacent healthy tissue to acceptable limits. The method starts at step 210 with the establishment of a cost function for the treatment volume. As mentioned above, a treatment volume is the entire volume that is irradiated in connection with the implementation of a treatment plan. A cost function is an objective function that models the dose that each portion of the treatment volume should receive, subject to constraints. For example, in a treatment volume that contains a tumor and an organ at risk (OAR), the clinician will generally prescribe that the tumor receive at least a certain minimum dose, while at the same time prescribing that the OAR receive no more than another maximum dose. The corresponding cost function is based on these minimum and maximum doses.

One exemplary way of defining an objective cost function is by representing each organ or tumor by a group of points or voxels distributed within the organ or tumor. Alternatively, they can be represented as a volumetric objects, such as sets of contours or surfaces. A cost function can be established by assigning a cost to each point within the treatment volume, and summing the contributions of individual points. The cost function may be defined in terms of the amount of dose that each point within the treatment volume receives. One example of a cost function may be that the cost=(dose to point−dose level of constraint)^2*density of points at that dose level, if the dose to the point is larger than the constraint dose, and 0 if the dose to point is smaller than the constraint dose. This example of a cost function is only one possible cost function, and embodiments of the present invention are not limited to this example. Various cost functions are known to those skilled in the art.

The cost function can be generally related to the amount of radiation, or dose, that each point within the treatment volume receives. Methods of calculating the dose received by a point within a treatment volume are well known and several have been described above. The method continues on at step 220 wherein the gradients of the cost function are calculated with respect to the dose, and those gradients are back projected to an optimization surface. The gradient of the cost function is the dose derivative of the cost function. Back projection of the cost gradients to an optimization surface may be better understood by way of the following example.

In an exemplary IMRT treatment plan, radiation may be delivered to a treatment volume using a multi-leaf collimator (MLC). As described above, an MLC comprises a plurality of individually moveable leaves capable of blocking radiation. Radiation may be delivered to a the treatment volume through the openings in the leaves. All bottom edges of the leaves of the MLC reside in a single plane and the radiation that passes through the MLC can be approximated as spreading from that plane. A treatment plan may be optimized by adjusting the position of the leaves of the MLC, and as such, the plane that is established with respect to the MLC leaves may be viewed as one example of an optimization surface.

Although the above example describes the use of an MLC and the plane being formed by the MLC leaves as being an optimization surface, embodiments of the present invention are in no way limited to planes, or to MLC leaves. For example, in another exemplary embodiment, such as in arc treatment, the optimization surface may be a curved surface, as defined by the rotation of the gantry around the treatment volume. In yet further embodiments, the surface may be defined as one that is created from movement of the treatment couch. All trajectory based treatment parameters may define a surface through which the treatment parameters may be optimized.

Continuing with this exemplary embodiment at step 230, after the cost function gradients have been back projected into the plane of the MLC, optimization of leaf positions may now occur. In this exemplary embodiment, the plane of the MLC leaves can be represented as a two dimensional matrix. Cost gradients that project back to the same matrix elements can be summed. Once this has occurred, the cost gradients may be normalized based on the treatment parameter that is being optimized. In this exemplary embodiment, normalization may comprise grouping matrix elements that are dependent on each other through the machine parameter being optimized. For example, because the leaf pairs of an MLC can not overlap, matrix elements that correspond to a given leaf pair may be grouped, because those matrix elements are dependent on changes in position of the leaf pair. Matrix elements within the group compete against each other for leaf movement.

Competition within groups can be described as the preference of the groups for changes in a machine parameter. Continuing with the above example, one group may comprise positions where the leaves are open and another group may comprise positions where the leaves are closed. It might be the case that in certain positions where the leaves are closed, the treatment volume requires additional dose. As such, that group would have a preference that the treatment parameter, the position of the leaves, be adjusted such that the leaves are opened. Similarly, the group comprising positions where the leaves are currently open may be receiving too much dose, and as such the preference of that group would be to close the leaves.

After the projection matrix has been calculated, the expected best position of the MLC leaves can be searched throughout the matrix. One exemplary method for performing such a search is to find an MLC leaf position that minimizes cost gradients within the opening, and maximizes the cost gradients outside the opening. Any number of additional methods of optimizing the leaf positions based on the gradient information may also be used. Because the gradient projection information is obtained by calculating the gradients of the cost function with respect to the dose, and not by using gradients calculated with respect to machine parameters, such as leaf position, the calculation is straightforward, and requires less time and computational resources.

In some embodiments it may be desirable to limit the amount that the leaves of the MLC may move in response to searching the matrix for the optimum leaf position. At step 240, utilizing the gradient back projection information, an optimum position for leaf positioning can be determined. Additional factors may be added into the function that models the cost gradients. For example, such an additional factor may comprise adding the sum of the distances the leaves must move to limit leaf movement. Moving the leaves over long distances would thereby have less of an effect on minimizing the cost function in comparison to changes in leaf position requiring less movement. Another exemplary factor may be adding the distance an individual leaf moves during a single iteration of the optimization. Large changes in individual leaf positions between iterations would have the effect of increasing the cost function and would thus be disfavored. Although this exemplary embodiment has referred to leaf movements, it would be clear to one of skill in the art that applying a weighting factor to other variable treatment parameters can also be used.

After the matrix has been searched for the optimum treatment machine parameters, a substantially new dose calculation, based on the newly calculated optimum machine parameters, may be made to evaluate the effect that the new parameters have on the dose that is received by the treatment volume. In some cases, the outcome may be an improvement and in other cases, it may result in a plan that is worse than the original. Utilizing standard search algorithms, such as simulated annealing, the new plan may be accepted or rejected. The entire process starting at 220 may then be repeated until an endpoint has been reached. The endpoint can be number of iterations completed, time, user interface signal, or the like. If the endpoint at step 250 has not been reached, the process repeats at step 220. If the endpoint has been reached, and thus a treatment plan that is optimized to an acceptable level has been reached, the treatment plan may then be delivered to a treatment volume.

Figure 3:
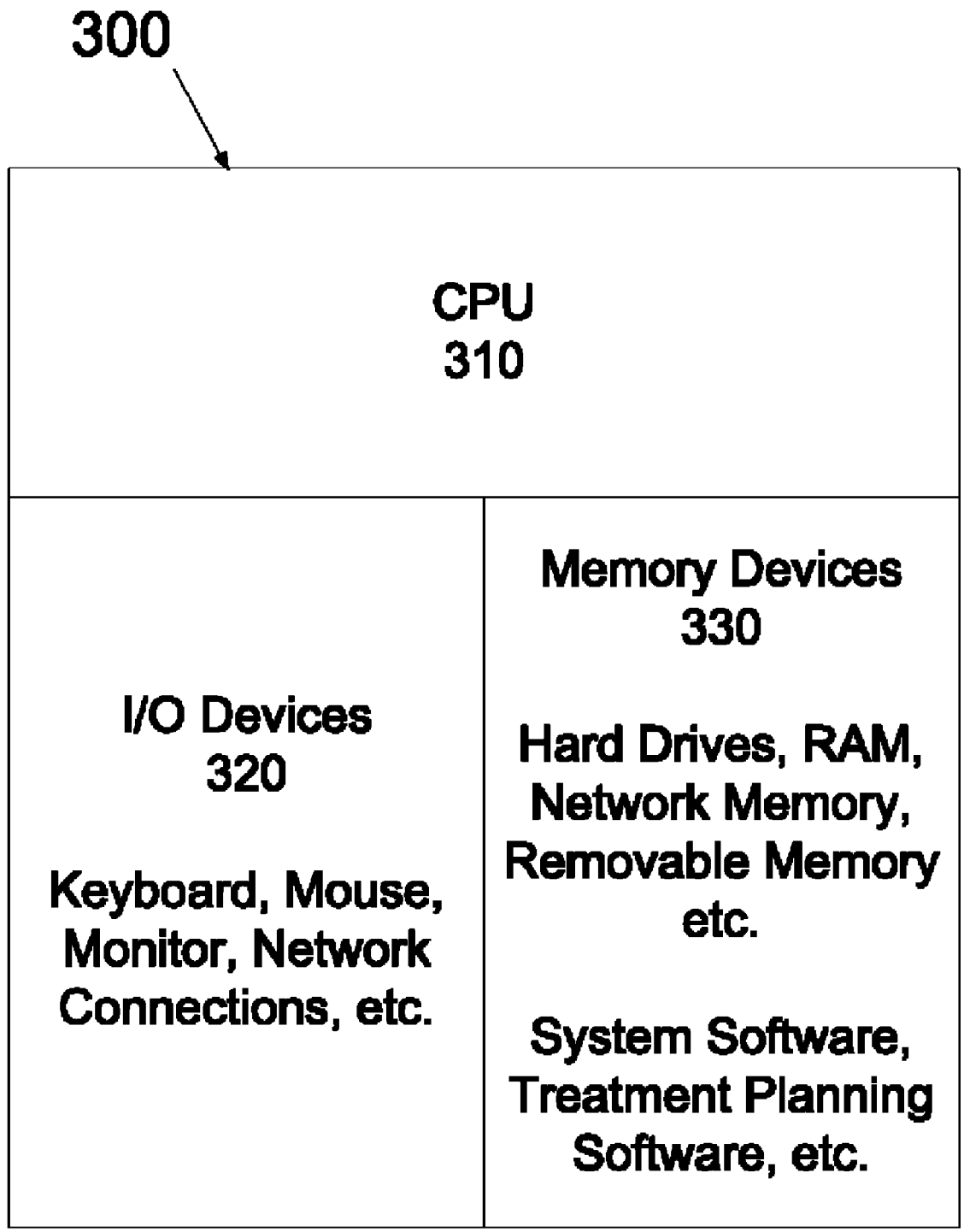
FIG. 3 is a block diagram of a treatment planning system in accordance with the present invention.

FIG. 3 represents a treatment planning system 300 in accordance with the present invention. Treatment planning system 300 comprises a computer system having a central processing unit (CPU) 310 bidirectionally connected to various I/O devices 320, such as one or more keyboards, pointing devices, monitors, network connections, etc., and bidirectionally connected to various memory devices 330, such as one or more hard disks, random access memory, flash memory and/or remote memory devices accessed over a local or wide area computer network. In some instances memory devices are considered to be I/O devices. However, for convenience they are treated separately herein. Memory devices 330 comprise one or more tangible media for storing various system software programs. Collectively, CPU 310, I/O devices 320 and memory devices 330 constitute a computing system, which may additionally include other conventional elements typically found in computing systems.

According to the present invention, I/O devices 320 include one or more data input devices for entering and patient data, for example, information about the tumor to be treated and about adjacent tissue structure, the prescribed dose to applied to the tumor, and the maximum radiation dose that can be tolerated by adjacent organs. Such patient data may comprise images from CT or MRI scans showing such structures. In one embodiment, I/O devices 320 comprise hardware and/or software tools to allow the system operator to digitize boundary and other information about such structures for use in treatment planning.

Software stored in memory devices 330 is loaded and processed in the computer system in any conventional manner. In accordance with the present invention, the software stored in memory devices 330 comprises software for optimizing a treatment plan for irradiating a target volume using a radiation therapy system having a multileaf collimator and capable of irradiating a treatment volume from a plurality of angles. The treatment planning software includes algorithms, such as gradient back projection algorithms, necessary to implement the methods as described in FIG. 2. As indicated above in connection with FIG. 2, the software iteratively repeats machine parameter optimization until an endpoint criteria is reached.

In a preferred embodiment the treatment planning system software further comprises an algorithm for translating the results of an optimized treatment plan into instructions for operating the radiation therapy system by controlling the positioning of the leaves of the multileaf collimator and the angle of irradiation. Treatment planning system can either be directly connected to system computer which controls the radiation system, the control instructions can be downloaded into the radiation system controller via a local or wide area network connection, or in any other known manner.

The embodiments described above are illustrative of the present invention and are not intended to limit the scope of the invention to the particular embodiments described. Accordingly, while one or more embodiments of the invention have been illustrated and described, it will be appreciated that various changes can be made therein without departing from the spirit or essential characteristics thereof. Accordingly, the disclosures and descriptions herein are not intended to be limiting of the scope of the invention, which is set forth in the following claims.

What is claimed is:

1. A method of optimizing a treatment plan for irradiating a treatment volume within a patient, comprising:
    establishing at least one treatment parameter;
    establishing a cost function corresponding to a treatment volume, wherein the treatment volume includes a target volume intended to receive a therapeutic dose of radiation and a non-target volume intended to receive a smaller dose of radiation, wherein the cost function is responsive to the radiation dose received by the treatment volume;
    back-projecting a plurality of gradients of said cost function to an optimization surface, wherein said gradients are responsive to changes in said at least one treatment parameter and wherein said optimization surface is defined by said at least one treatment parameter; and
    changing said at least one treatment parameter, wherein said change in said at least one treatment parameter causes a corresponding change in said back projected gradients;
    wherein at least one of establishing at least one treatment parameter, back projecting a plurality of gradients, or changing said at least one treatment parameter is performed with a treatment planning computer.

2. The method of claim 1 further comprising normalizing said back-projected gradients within said optimization surface.

3. The method of claim 2 wherein normalizing said back projection gradients comprises grouping said back projection gradients into at least two groups, wherein said groups are responsive to changes in said at least one treatment parameter.

4. The method of claim 3, wherein said at least one treatment parameter is changed to optimize said groups, wherein optimizing said groups comprises minimizing a sum of said back projection gradients within said groups.

5. The method of claim 4 wherein the sum of said back projected gradients further include an additional factor proportional to a magnitude of the change in said at least one treatment parameter, wherein said factor increases the sum of said back projection gradients, whereby minimizing the sum of said back projection gradients within said groups is favored by smaller changes in said at least one treatment parameter.

6. The method of claim 5 wherein the steps are iterated a plurality of times.

7. The method of claim 6 wherein said treatment plan comprises Intensity Modulated Radiation Therapy.

8. The method of claim 6 wherein said treatment plan comprises Arc treatment.

9. The method of claim 5 wherein the at least one treatment parameter is a treatment machine parameter and said gradients of said cost function are not calculated with respect to said treatment machine parameter.

10. The method of claim 5 wherein the at least one treatment parameter is a treatment machine parameter and said gradients of said cost function are calculated with respect to said radiation dose received by said treatment volume.

11. A method for generating a radiation therapy treatment plan comprising:
    establishing at least one treatment machine parameter;
    establishing a cost function corresponding to a treatment volume, wherein the treatment volume includes a target volume intended to receive a therapeutic dose of radiation and a non-target volume intended to receive a smaller dose of radiation, wherein the cost function is responsive to the radiation dose received by the treatment volume;

back projecting gradients of said cost function to a surface, wherein said surface is defined by said at least one treatment machine parameter, wherein said gradients are calculated with respect to said radiation dose, and wherein said gradients are responsive to changes in said at least one treatment machine parameter; and changing said at least one treatment machine parameter, wherein said change in said at least one treatment machine parameter causes a corresponding change in said back projected gradients;

wherein at least one of establishing at least one treatment machine parameter, back projecting gradients of said cost function, or changing said at least one treatment machine parameter is performed with a treatment planning computer.

12. The method of claim 11 further comprising:
segmenting said surface into a matrix, wherein said matrix has at least two elements;
aggregating said back projection gradients that project into each of said at least two matrix elements;
grouping said matrix elements into at least two groups, wherein said groups contain matrix elements that compete for changes in said treatment machine parameter.

13. The method of claim 12 wherein said at least one treatment machine parameter is changed to minimize the sum of said back projected gradients within said groups.

14. The method of claim 13 wherein the sum of said back projected gradients further include an additional factor proportional to a magnitude of the change in said at least one treatment machine parameter, wherein said factor increases the sum of said back projection gradients, whereby minimizing the sum of said back projection gradients within said groups is favored by smaller changes in said at least one treatment machine parameter.

15. The method of claim 14 wherein the steps are iterated a plurality of times.

16. A method for optimizing leaf positions of a multi-leaf collimator used to deliver a radiation treatment plan to a patient comprising:
establishing an initial position for a plurality of leaves of a multi-leaf collimator;
establishing a cost function corresponding to a treatment volume, wherein the treatment volume includes a target volume intended to receive a therapeutic dose of radiation and a non-target volume intended to receive a smaller dose of radiation, wherein the cost function is responsive to the radiation dose received by the treatment volume;
back projecting gradients of said cost function to a plane established by the leaves of said multi-leaf collimator, wherein said gradients are calculated with respect to said radiation dose and wherein said gradients are responsive to changes in said leaf positions; and
changing positions of said leaves in said multi leaf collimator, wherein said change in said positions of said leaves of said multi leaf collimator causes a corresponding change in said back projected gradients.

17. The method of claim 16 further comprising:
establishing a matrix in said plane, wherein each element of said matrix corresponds to a position of a leaf in said multi leaf collimator;
summing all back projected gradients of said cost function that back project to the same matrix element;
grouping said matrix elements into at least two groups, wherein said groups contain matrix elements that compete for changes in said positions of said leaves in said multi leaf collimator.

18. The method of claim 17 wherein said position of said leaves in said multi leaf collimator is changed to minimize the sum of said back projected gradients within said groups.

19. The method of claim 18 wherein the sum of said back projected gradients further include an additional factor proportional to a distance traveled by said leaves of said multi leaf collimator, wherein said factor increases the sum of said back projection gradients, whereby minimizing the sum of said back projection gradients within said groups is favored by smaller distances traveled by said leaves of said multi leaf collimator.

20. The method of claim 19 wherein the steps are iterated a plurality of times.

21. A non-transitory computer readable medium storing thereon a program for execution by a computer, the program having code for performing the steps of:
establishing at least one treatment parameter;
establishing a cost function corresponding to a treatment volume, wherein the treatment volume includes a target volume intended to receive a therapeutic dose of radiation and a non-target volume intended to receive a smaller dose of radiation, wherein the cost function is responsive to the radiation dose received by the treatment volume;
back-projecting a plurality of gradients of said cost function to an optimization surface, wherein said gradients are responsive to changes in said at least one treatment parameter and wherein said optimization surface is defined by said at least one treatment parameter; and
changing said at least one treatment parameter, wherein said change in said at least one treatment parameter causes a corresponding change in said back projected gradients.

22. The non-transitory computer readable medium of claim 21 further comprising:
normalizing said back-projected gradients within said optimization surface, wherein normalizing said back projected gradients comprises grouping said back projection gradients into at least two groups, wherein said groups are responsive to changes in said at least one treatment parameter.

23. The non-transitory computer readable medium of claim 22, wherein said at least one treatment parameter is changed to optimize said groups, wherein optimizing said groups comprises minimizing a sum of said back projection gradients within said groups.

24. The non-transitory computer readable medium of claim 23, wherein the sum of said back projected gradients further include an additional factor proportional to a magnitude of the change in said at least one treatment parameter, wherein said factor increases the sum of said back projection gradients, whereby minimizing the sum of said back projection gradients within said groups is favored by smaller changes in said at least one treatment parameter.

* * * * *